(12) United States Patent
Volpicelli

(10) Patent No.: US 11,167,112 B2
(45) Date of Patent: Nov. 9, 2021

(54) CATHETER SAFETY PRODUCT

(71) Applicant: Kevin Lee Gardner, Frisco, TX (US)

(72) Inventor: Antonio Volpicelli, Addison, TX (US)

(73) Assignee: Kare Devices, LLC, Frisco, TX (US)

( * ) Notice: Subject to any disclaimer, the term of this patent is extended or adjusted under 35 U.S.C. 154(b) by 0 days.

(21) Appl. No.: 14/720,764

(22) Filed: May 23, 2015

(65) Prior Publication Data

US 2015/0335863 A1 Nov. 26, 2015

Related U.S. Application Data

(60) Provisional application No. 62/002,582, filed on May 23, 2014.

(51) Int. Cl.
*A61M 25/02* (2006.01)
*A61J 15/00* (2006.01)

(52) U.S. Cl.
CPC .......... *A61M 25/02* (2013.01); *A61J 15/0053* (2013.01); *A61J 15/0061* (2013.01); *A61M 2025/0253* (2013.01)

(58) Field of Classification Search
CPC ............ A61M 25/02; A61M 2025/0253; A61J 15/0053; A61J 15/0061
See application file for complete search history.

(56) References Cited

U.S. PATENT DOCUMENTS

| | | | | |
|---|---|---|---|---|
| 3,430,300 A | * | 3/1969 | Doan | A61M 25/02 24/304 |
| 3,826,254 A | * | 7/1974 | Mellor | A61M 25/02 604/180 |
| 2006/0041233 A1 | * | 2/2006 | Bowen | A61M 25/02 604/180 |

* cited by examiner

*Primary Examiner* — Lauren P Farrar
(74) *Attorney, Agent, or Firm* — William S. Parks

(57) ABSTRACT

A catheter protection device and method for securing a catheter to a patient's body to prevent the unauthorized and possibly traumatic removal of a catheter. The device is thin, breathable and not easily removed by an agitated or mentally incompetent patient. The device is constructed of a base, adhesives, and a sleeve. The edges of the base each contain a section of adhesive wherein mid-portion of the base remains uncovered by adhesive. The open sleeve is permanently attached to an edge of the base. Once a catheter has been placed in an open sleeve, the sleeve will be folded such that the rear portion of the sleeve attached to the nearest edge of the base creating a closed sleeve surrounding the catheter. The catheter protection device may be placed against a patient's body with the adhesive edges of the base and an adhesive covered catheter sleeve adjacent to a patient.

10 Claims, 4 Drawing Sheets

CATHETER SAFETY PRODUCT

TECHNICAL FIELD

The present application relates generally to medical care technology and more particularly to a protection for a catheter.

BACKGROUND

A catheter is typically a thin, flexible tube that may be utilized in treatment of disease or during surgery. Catheters may be inserted into a body cavity, duct or vessel in order to facilitate the removal of bodily fluids or to provide for administration intravenous fluids. Some catheters include an inflatable balloon-like device at one end, which prevents the catheter tube from slipping out of the position within the body. A catheter may be inserted into the uretha or kidneys in order to drain urine from a patient who is unconscious, immobilized or otherwise unable to transport himself or herself to the bathroom facility. A catheter may also be used to administer intravenous fluids to a patient.

Oftentimes, patients will become agitated or annoyed by the insertion or continued placement of the catheter within their bodies and attempt to forcefully remove said catheter. Patients with any number of ailments, including but not limited to, dementia, Alzheimer's, mental illness, stroke, seizures, hypertension, alcoholism, concussions, sepsis, among others, may have reduced tolerance for pain or annoyance caused by the insertion of a catheter. Patients with kidney disease that require a catheter to be placed under the chest for drainage possibly run the risk of accidental catheter removal due to excessive movement leading to infectious complications. Additionally, patients with a Nasogastric catheter or tube (NG), which aids in nutritional support or aspiration of stomach contents, may also pull at the NG tube due to the discomfort and pain it causes. Patients with a urinary catheter and a drainage bag, especially women, oftentimes experience discomfort and agitation from a free-wielding tube hanging between their pubic area and their drainage lap bag.

Patients often attempt to forcefully remove catheters from their body. These types of forceful actions may cause severe injuries to the patient such as internal bleeding, tearing of tissues, urinary tract infections, lost fragments of the balloon located inside the body cavity to secure the catheter in place may lead to infection, or long term damage to the urethra. Food and fecal matter may also contaminate the exposed catheter leading to urinary tract infections which could lead to serious complications in patients.

In order to address these issues, medical professionals have typically restrained the arms of the patient to prevent removal of the catheter. A less drastic solution has been to attach the catheter to the patient's body. However, patients are still able to grasp the exposed portions of the catheter and attempt an unauthorized removal. The exposed catheter is prone to facilitating infection by collecting germs, food and fecal matter thereby exposing the patient to a substantially increased risk of infection. The catheter safety device prevents an agitated or mentally compromised patient from causing additional harm or medical issues due to the unauthorized and destructive removal of a catheter. The catheter safety device provides comfort to patients, especially women, by securing the free-hanging tube from their urinary catheter. It also provides greater comfort and added protection from tearing and infection in patients with NG and intravenous catheters or tubes.

SUMMARY OF THE DISCLOSURE

For a more complete understanding of the present disclosure and its advantages, reference, is now made to the following description taken in conjunction with the accompanying drawings, in which like reference numerals represent like parts. The catheter safety device ("CSD") prevents the unauthorized and possibly traumatic removal of a catheter from a user's body. The device is thin, breathable and not easily removed by an agitated or mentally incompetent patient. The CSD is comprised of a base for securing the CSD to the patient's body and an attached sleeve for securing, the catheter within the CSD. The CSD includes adhesives on the base and sleeve in order to maintain the connection between the patient's body and the CSD. The CSD can be used on any appendage, various sections of the torso, the head and neck region, or any other section of the body where a medical professional may place a catheter or where a catheter is required for treatment.

The edges of the base each contain a section of adhesive wherein a mid-portion of the base remains uncovered by adhesive. The open sleeve is permanently attached to an edge of the base. Once a catheter has been placed in an open sleeve, the sleeve will be folded such that the rear portion of the sleeve attached to the nearest edge of the base creating a closed sleeve surrounding the catheter. The catheter safety device may be placed against a patient's body with the adhesive edges of the base and an adhesive covered catheter sleeve adjacent to a patient.

The CSD is constructed of a thin, flexible material such as SMS (spunbond+meltblown+spunbond) non-woven fabric with medical repellence (anti-alcohol, anti-blood, anti-oil) and anti-static, anti-mildew, super-soft, hydrophobic properties; SMMS (spunbond+meltblown+meltblown spunbond) non-woven fabric with medical repellence and anti-static, anti-mildew, super-soft, hydrophobic properties; or non-woven polypropylene treated to have medical repellence and anti-static, anti-mildew, super-soft, hydrophobic properties. In this embodiment, the base is constructed of SMS (spunbond+meltblown+spunbond) non-woven fabric with medical repellence (anti-alcohol, anti-blood, anti-oil) and anti-static, anti-mildew, super-soft, hydrophobic properties, so that the CSD is breathable, waterproof and allows air to circulate adjacent to the skin surface, which prevents moisture accumulation or excessive adhesive on the patient's skin. Additionally, due to the thinness of the CSD material, the CSD is not easily perceived or removed by an agitated patient.

The adhesive used to securely attach the CSD to the patient's body may be any variety of medical grade adhesives such as double-sided tape, pressure sensitive adhesives, polyolefins, polystyrenes, polycarbonates, acrylics, silicone rubber, polyethylenes, polypropylenes, and synthetic rubbers, epoxies, and styrene block copolymers. The adhesive depicted in this embodiment is double-sided adhesive strip or tape with an adhesive covering, but could be any adhesive suitable for use on a patient. Once the adhesive coverings are removed, the entire CSD will be attached to a patient's body with all exposed adhesive sections touching the patient's skin. The benefit of double sided adhesive strip with a removable adhesive covering, or a similar adhesive, is that unused CSD can be stacked atop one another and easily removed from said stack for patient use within seconds. Use of an exposed adhesive (i.e. an adhesive with its sticky surface uncovered) with CSD would cause stacks of CSD to stick to each other, possibly becoming useless and likely cumbersome to the medical professional. However, it is to be understood that an exposed adhesive can be used with the CSD but the use of such an adhesive will make likely cause difficulties for medical professionals working with multiple CSD.

In the present embodiment, which uses double sided adhesive tape, the adhesive coverings may be removed in one step or incrementally. The base adhesive may be individual strips for each side of the base component or a single strip of adhesive covering the edges of the base component. With regard the base covering composed of separate strips of adhesive, a user may remove the base adhesive covering nearest the sleeve, insert the catheter, fold the sleeve over the catheter, remove the sleeve adhesive covering and remaining base adhesive coverings and then attach the CSD to the patient. Alternatively, the user may remove all of the individual base adhesive coverings prior to creating the open sleeve, however, this may present difficulties with an unruly patient. With regard to the base covering composed of a single strip of base adhesive, the base adhesive may be removed from the entire base component in a single movement, the open sleeve folded over the catheter, the sleeve adhesive removed and then the CSD may be placed against the patient's body. Alternatively, the single strip of base adhesive covering may be removed partially to expose the edge of the base closest to the open sleeve, the catheter inserted into the open sleeve, the sleeve folded over the catheter, the sleeve adhesive covering removed, the remainder of the single strip of base adhesive covering removed to expose the remaining base adhesive, and then the CSD may be placed against the patient's skin. If the base adhesive is partially removed, the medical professional will have more control over the CSD and a greater likelihood of proper placement of the CSD, especially in cases of unruly or agitated patients. In an alternative embodiment, a closed sleeve may be attached to a base component. The catheter may be inserted into to the closed sleeve, the sleeve adhesive covering removed, the base adhesive covering removed and then the CSD may be placed against a patient's body.

The CSD may be quickly removed and replaced in slightly different locations on the body in order to allow the body's skin surfaces to air out while not covered with the CSD. Since the CSD is constructed of thin material, the agitated patient will have difficulty sensing the catheter against the skin and will have even greater difficulty locating a grasping point should the patient desire to tear the catheter from its proper position. In addition, a patient in the horizontal position will have great difficulty reaching the exposed part of the catheter within the CSD. Medical professionals using the CSD, will see a marked reduction in urinary tract infections ("UTI") in patients since the catheter will be protected, by virtue of placement in the CSD sleeve, from food, fecal, and any other foreign matter, thereby reducing contamination and the associated risk of infection. Additionally, the waterproof nature of the CSD, the catheter will not be exposed to any moisture or contaminants while the medical professional provides the patient with a sponge bath.

An additional benefit of the CSD is the increased comfort for the patient due to the soft and breathable nature of the CSD material and the attachment of the CSD to the body keeping the catheter in place within the body while still allowing for the movement of the catheter within the sleeve. There will be additional savings in overall healthcare costs since patients will suffer fewer infections and complications created by the unauthorized and/or improper removal of catheters. Medical facilities will also realize decreases in the time required for medical professionals to insert and re-insert catheters haphazardly removed by patients. For maximum safety and comfort, the CSD should be changed every 3-4 days.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
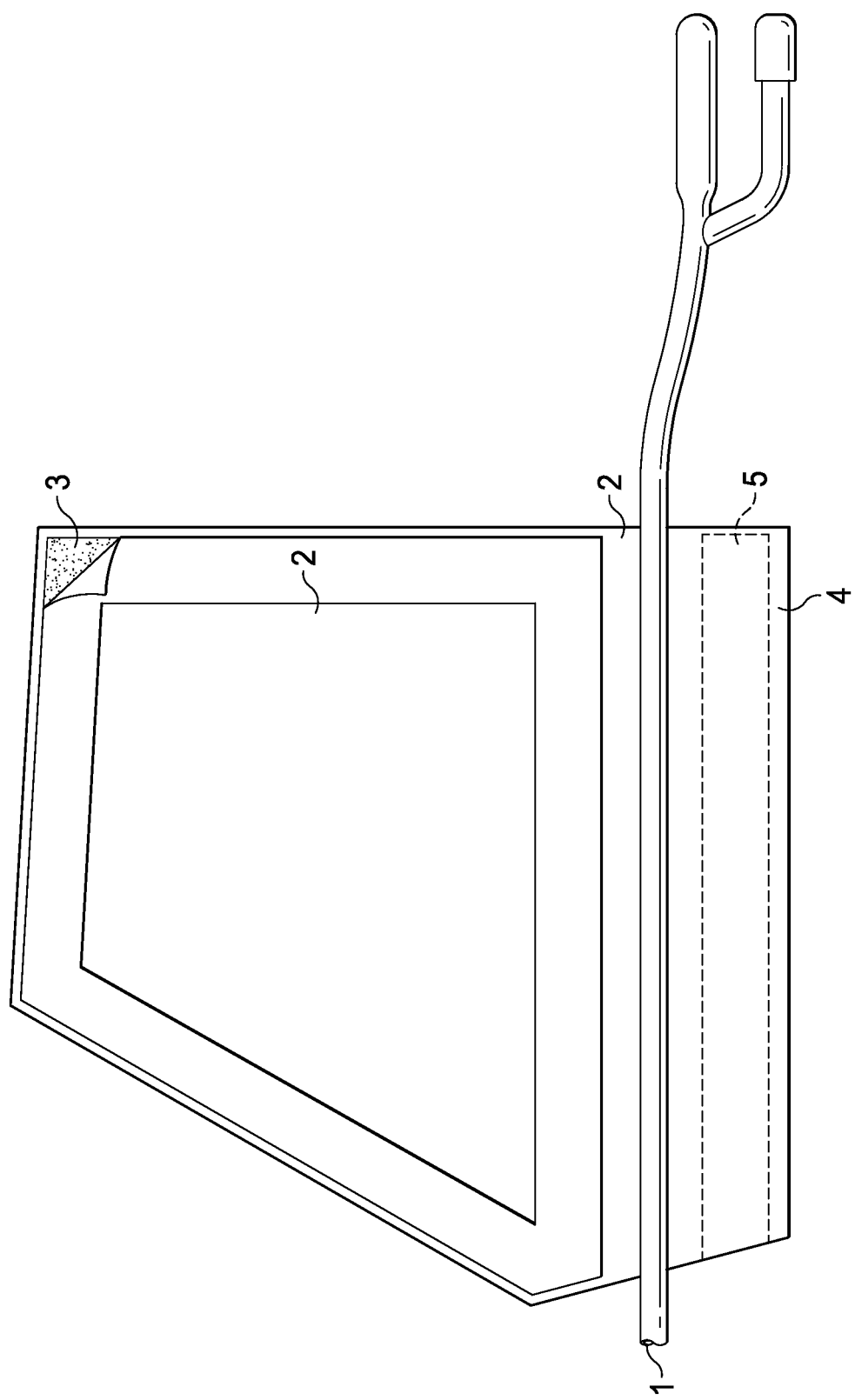
FIG. 1 is a front view of the CSD, with a catheter in the open sleeve;
    Ref 1 is a catheter
    Ref 2 is the base of the CSD;
    Ref 3 is the base adhesive;
    Ref 4 is the sleeve of the CSD;
    Ref 5 is the sleeve adhesive.
Figure 2:
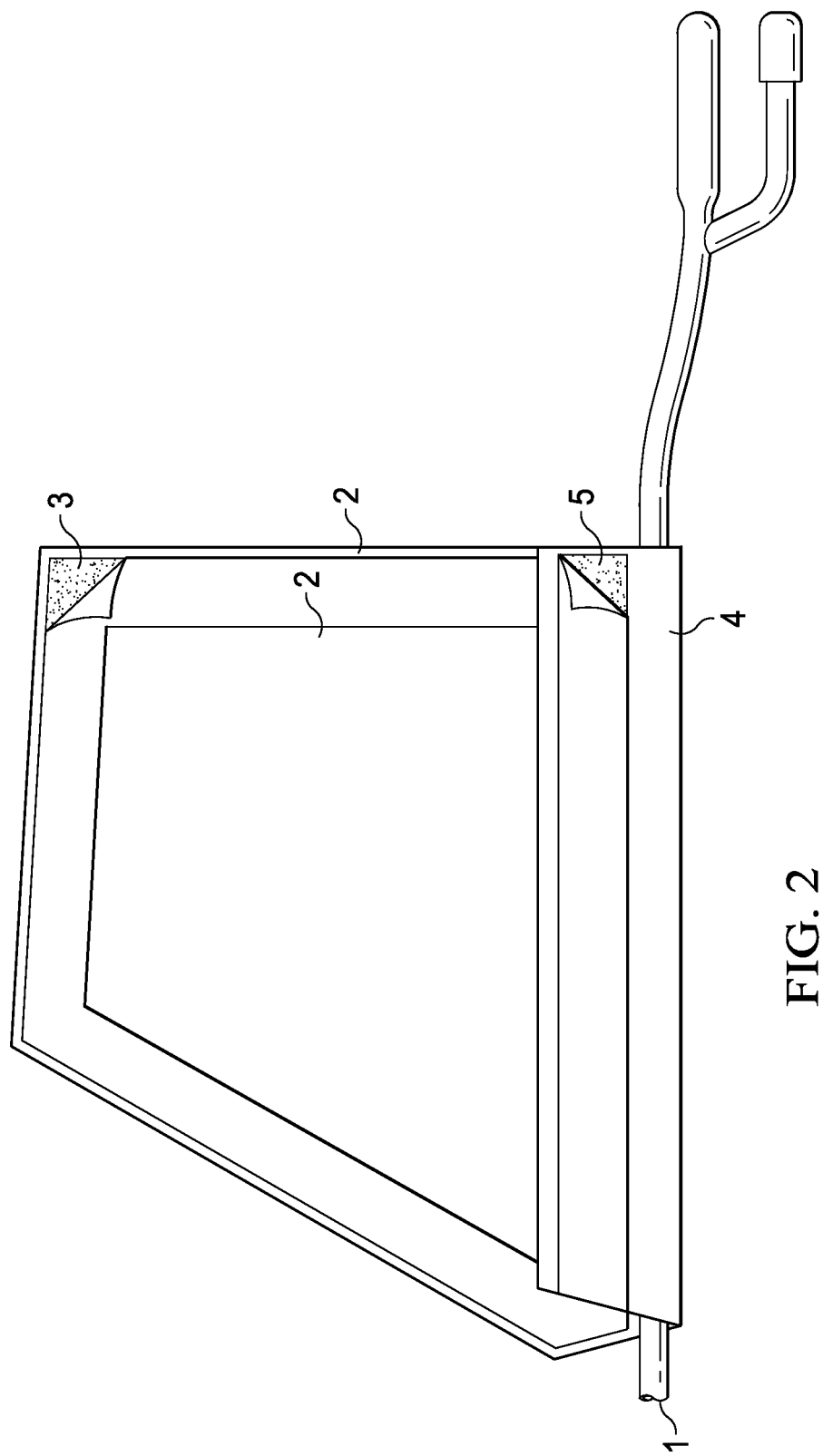
FIG. 2 is a front view of the CSD, with a catheter in the closed sleeve;
    Ref 1 is a catheter
    Ref 2 is the base of the CSD;
    Ref 3 is the base adhesive;
    Ref 4 is the sleeve of the CSD;
    Ref 5 is the sleeve adhesive.
Figure 3:
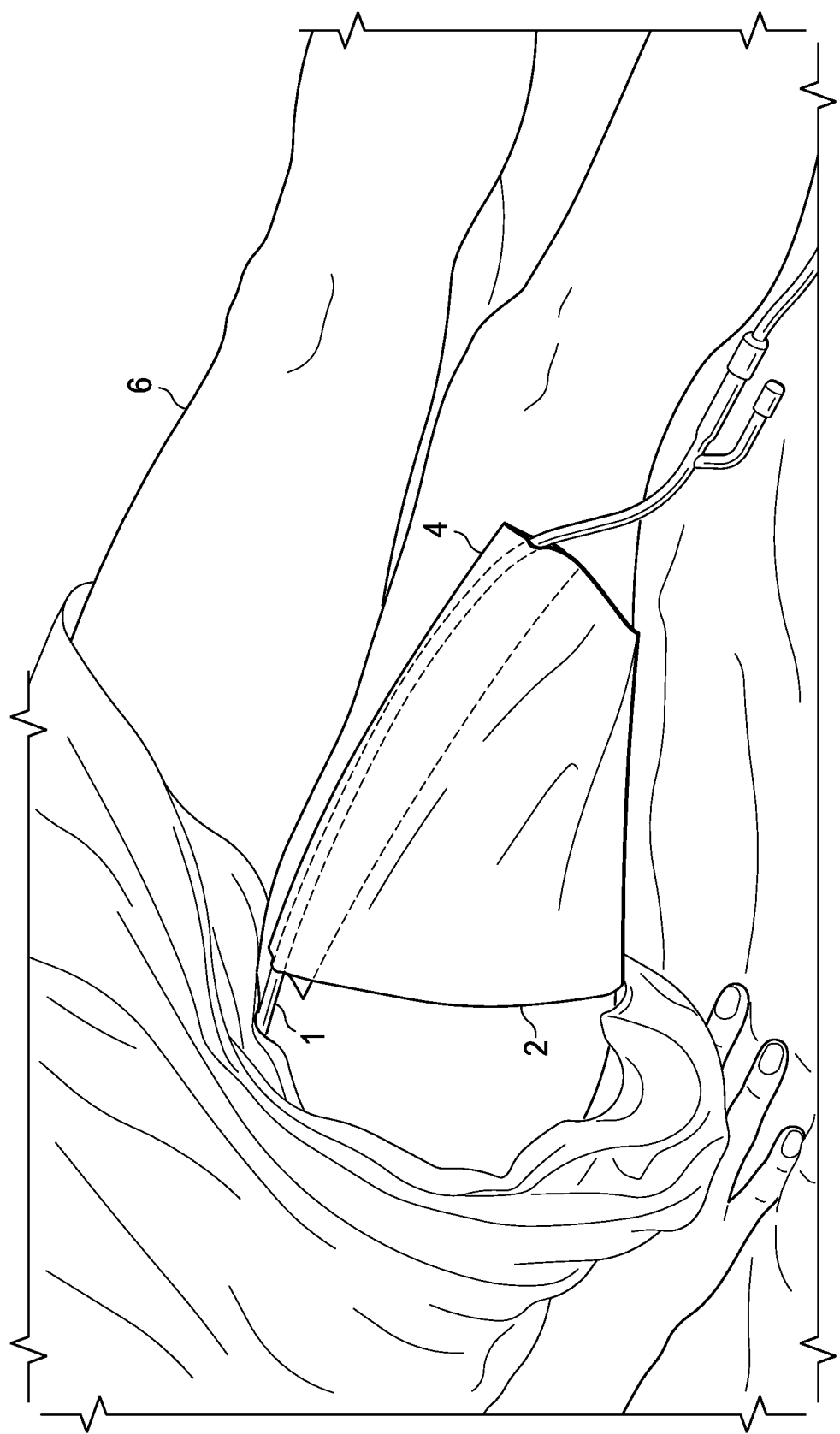
FIG. 3 is a rear view of the CSD, with a catheter, affixed to a patient's body;
    Ref 1 is a catheter
    Ref 2 is the base of the CSD;
    Ref 4 is the sleeve of the CSD;
    Ref 6 is the patient's body.

FIGS. 1 through 3, discussed below, and the various embodiments used to describe the principles of the present disclosure are by way of illustration only and should not be construed in any way to limit the scope of the invention. Those skilled in the art will understand that these principles may be implemented in any type of suitably arranged device or system.

FIG. 1 illustrates a front view of the CSD, with an open sleeve. The edges of the base 2 each contain a strip of base adhesive 3 wherein the mid-portion of the base remains uncovered by base adhesive. Since the adhesive coverings are limited to the edges of the base 2, the CSD remains breathable, allowing air to circulate and contact the user's skin. The sleeve 4 is permanently attached to an edge of the base 2. In an open state, the sleeve adhesive 5 is not visible. Once a catheter 1 has been placed in an open sleeve 4, the base adhesive covers will be removed and the sleeve 4 will be folded over such that the further edge of the open sleeve 4 will attach to the nearest edge of the base 2, creating a closed sleeve 4 for securing the catheter 1. With the catheter 1 secured in the closed sleeve 4, the catheter protection device may be placed against a patient's body with the removal of the adhesive covering the edges of the base 2 and an adhesive covered catheter sleeve adjacent to a patient.

Although FIG. 1 depicts specific dimensions for the base, the dimensions could be altered to any desirable size for a particular patient. In fact, a large CSD could be trimmed to smaller dimensions to accommodate various patients.

FIG. 2 illustrates a front view of the CSD, with a closed sleeve 4. The distal edge of the sleeve 4 is now attached to the base adhesive 3 on the nearest base edge. The catheter 1 is now secure within the closed sleeve 4 of the CSD. The catheter 1 is not adhered to the sleeve 4 and is able to move within the sleeve. The remaining base edges are also covered with base adhesive 3. In order to utilize the CSD, the base adhesive covers and the sleeve adhesive covers will be removed and discarded. The entire CSD will be attached to a patient's body with all exposed adhesive sections touching the patient's skin. Since the CSD is constructed of thin material, the agitated patient will have difficulty sensing the catheter against the skin and will have even greater difficulty locating a grasping point should the patient desire to tear the catheter from its proper position. The adhesive depicted in this embodiment is double-sided adhesive strip with an adhesive covering, but could be any adhesive suitable for use on a patient.

FIG. 3 illustrates a CSD in position on a patient's body. Once a catheter 1 has been inserted inside a patient, a portion of the catheter 1 will remain exposed outside the body 6. The exposed portion of the catheter 1 will be placed inside the open sleeve 4. The sleeve 4 will be folded over the catheter 1 to secure the position of the catheter 1. The distal edge of the sleeve 4 will be attached to the near edge of the base component of the CSD via the base adhesive. A sleeve adhesive will be on the exposed edge of the sleeve. Once the medical professional is ready to attach the CSD to the patient's body 6, the adhesive covers will be removed. The CSD will be placed against the skin of the patient by the medical professional.

Figure 4:
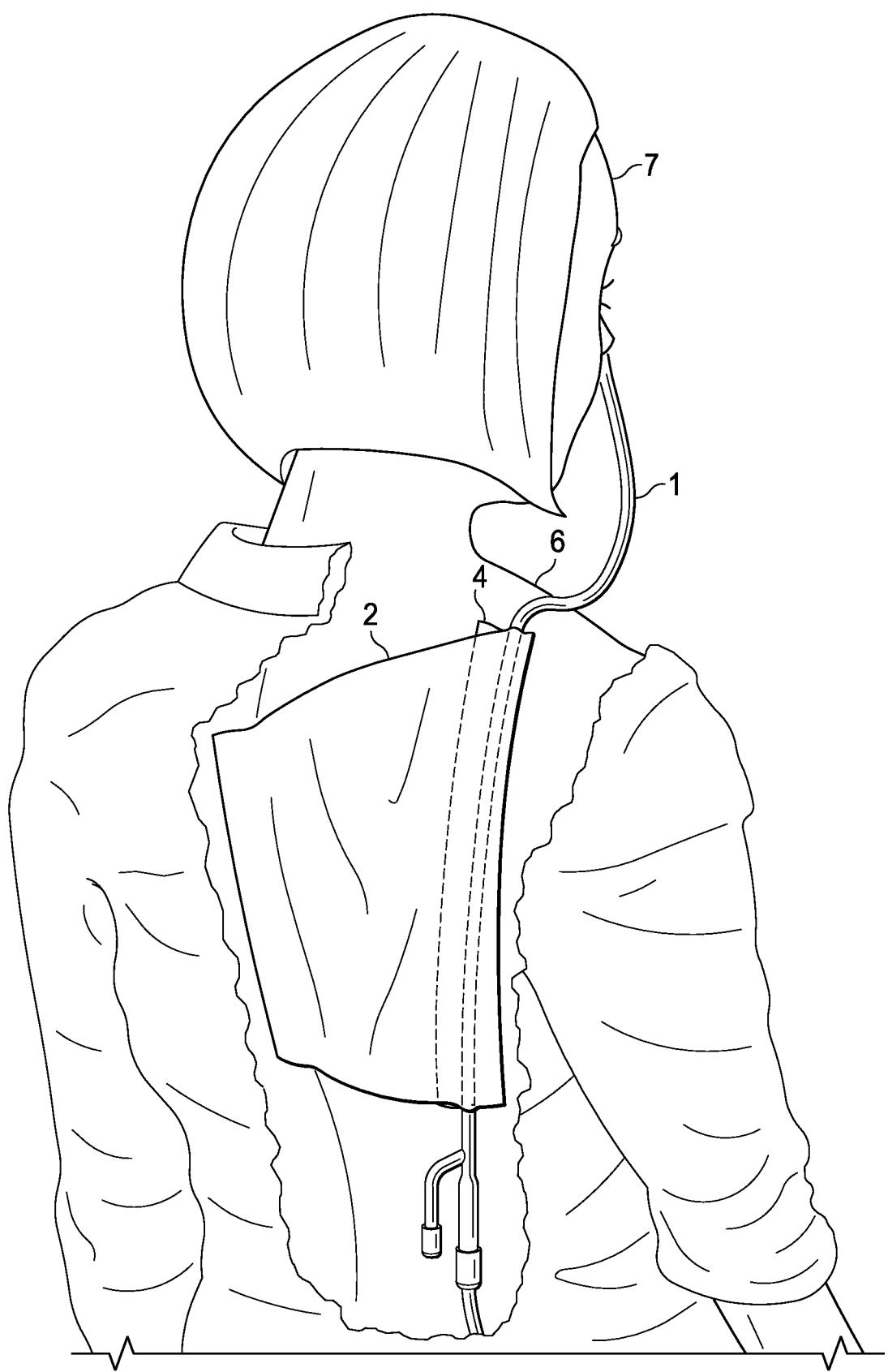
FIG. 4
    Ref 1 is a catheter
    Ref 2 is the base of the CSD;
    Ref 4 is the sleeve of the CSD;
    Ref 6 is the patient's body;
    Ref 7 is the patient's head.

FIG. 4 illustrates a CSD in position on a patient's head 7. Once a catheter 1 has been inserted inside a patient, a portion of the catheter 1 will remain exposed outside the body 6. The exposed portion of the catheter 1 will be placed inside the open sleeve 4. The sleeve 4 will be folded over the catheter 1 to secure the position of the catheter 1. The distal edge of the sleeve 4 will be attached to the near edge of the base component of the CSD via the base adhesive. A sleeve adhesive will be on the exposed edge of the sleeve. Once the medical professional is ready to attach the CSD to the patient's body 6, the adhesive covers will be removed. The CSD will be placed against the skin of the patient by the medical professional.

The various components and operations shown in each of FIGS. 1 through 4 may be incorporated in other figures without departing from the scope of this disclosure. Modifications, additions, or omissions may be made to the systems, apparatuses, and methods described herein without departing from the scope of this disclosure. The components of the systems and apparatuses may be integrated or separated. Moreover, the operations of the systems and apparatuses may be performed by more, fewer, or other components. The methods may include more, fewer, or other operations. Additionally, operations may be performed in any suitable order. As used in this document, "each" refers to each member of a set or each member of a subset of a set.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of the disclosure, as defined by the following claims.

What is claimed is:

1. A catheter safety device comprising: i) a base and ii) a sleeve; wherein said base has a top side and a bottom side and comprises a mid-portion and a plurality of edges, and wherein said sleeve has a top side and a bottom side and is present as a foldable edge adjacent to and permanently attached to one of said plurality of edges of said base wherein said sleeve includes a sleeve adhesive present on said bottom side thereof with a protective removable covering present thereon; wherein said plurality of edges of said base includes strips of base adhesive present thereon, wherein said mid-portion of said base is free from adhesives, wherein said top side of said base further comprises an adhesive strip configured parallel to said sleeve, and wherein said base adhesives present on said plurality of edges of said base include removable protective coverings and positioned on said top side thereof; wherein said sleeve is configured in an open state to fold around a catheter placed thereon and to attach to said top side of said base around said catheter in relation to said adhesive strip parallel to said sleeve whereupon said sleeve adhesive present on said bottom side thereof is positioned on the top side of said base in the same direction as said strips of base adhesive included on said plurality of edges of said base; and wherein, upon folding of said sleeve around said catheter, said catheter is free to move within said sleeve.

2. The catheter safety device of claim 1, wherein said plurality of edges of said base comprises four edges, wherein a first edge is covered by a first section of said base adhesive, wherein a second edge is covered by a second section of said base adhesive, wherein a third edge is covered by a third section of said base adhesive, and wherein a fourth edge is covered by a fourth section of said base adhesive.

3. The catheter safety device of claim 2, wherein said sleeve contains a front section and a rear section, and wherein said front section of said sleeve contains a first section of said sleeve adhesive.

4. The catheter safety device of claim 3, wherein said first edge of said base is adjacent to said first edge of said rear section of said sleeve in an open state.

5. The catheter safety device of claim 4, wherein said second edge of said rear section of said sleeve is attached to said first edge of said base covered by said first section of base adhesive, in a closed state, creating a secure position for a catheter.

6. A method of protecting a catheter with a catheter safety device of claim 2, said method steps comprising: removal of a first section of base adhesive covering from a said first section of base adhesive; placing a catheter on said sleeve; folding said sleeve such that an outer edge of said sleeve attaches to said first section of base adhesive; removal of a sleeve adhesive covering from said sleeve adhesive; removal of a second section of base adhesive covering from said second section of base adhesive; placing said catheter safety device against a user's body, wherein said catheter safety device adheres to said user's body in relation to said sleeve adhesive and said base adhesive, wherein air is allowed to circulate underneath said mid-portion of said base, and wherein said catheter within said folded sleeve is free to move therein.

7. The catheter safety device of claim 1, wherein said base is selected from the group consisting of: non-woven fabric, polypropylene fabric, polyethylene fibers, mesh, SMS, and SMMS.

8. The catheter safety device of claim 1, wherein said sleeve is selected from the group consisting of: non-woven fabric, polypropylene fabric, polyethylene fibers, mesh, and SMS.

9. The catheter safety device of claim 1, wherein said adhesive is selected from the group consisting of: double-sided tape, pressure sensitive adhesive, polyolefins, polystyrenes, polycarbonates, acrylics, silicone rubber, polyethylenes, polypropylenes, and synthetic rubbers, epoxies, and styrene block copolymers.

10. A method of protecting a catheter with said catheter safety device of claim 1, said method comprising: removal of said base adhesive coverings from said base adhesives; placing a catheter on said sleeve; folding said sleeve such that an outer edge of said sleeve attaches to an inner edge of said base adhesive; removal of said sleeve adhesive covering from said sleeve adhesive; and placing said catheter safety device against a user's body, wherein said catheter safety device adheres to said user's body in relation to said sleeve adhesive and said base adhesive, wherein air is allowed to circulate underneath said mid-portion of said base, and wherein said catheter within said folded sleeve is free to move therein.

\* \* \* \* \*